United States Patent [19]

Baumann et al.

[11] 4,240,979
[45] Dec. 23, 1980

[54] AROYLUREAS

[75] Inventors: Annegrit Baumann, Mannheim; Karl Kiehs, Lampertheim; Heinrich Adolphi, Limburgerhof; Karl-Heinz Koenig, Frankenthal, all of Fed. Rep. of Germany

[73] Assignee: BASF Aktiengesellschaft, Fed. Rep. of Germany

[21] Appl. No.: 71,552

[22] Filed: Aug. 30, 1979

[30] Foreign Application Priority Data

Sep. 11, 1978 [DE] Fed. Rep. of Germany ....... 2839462

[51] Int. Cl.³ .................... C07C 127/22; A01N 9/20
[52] U.S. Cl. ...................... 564/44; 424/275; 424/263; 424/322; 546/323; 549/72
[58] Field of Search .................................. 260/553 E

[56] References Cited

U.S. PATENT DOCUMENTS

| 4,013,717 | 3/1977 | Willinga et al. | 260/553 E |
| 4,085,226 | 4/1978 | Sirrenberg et al. | 260/553 E X |
| 4,089,975 | 5/1978 | Wade et al. | 260/553 E X |
| 4,139,636 | 2/1979 | Sirrenberg et al. | 424/322 |
| 4,162,330 | 7/1979 | Ehrenfreund | 260/553 E X |
| 4,170,657 | 10/1979 | Rigterink | 260/553 E X |

FOREIGN PATENT DOCUMENTS 1324293  7/1973  United Kingdom .

OTHER PUBLICATIONS

Neustadt, CA 85:77701s (1976).
DeMilo et al., J. Agric. Food Chem., vol. 26, pp. 164–166 (1978).

Primary Examiner—Thomas A. Waltz
Attorney, Agent, or Firm—Keil & Witherspoon

[57] ABSTRACT

Aroylureas of the formula

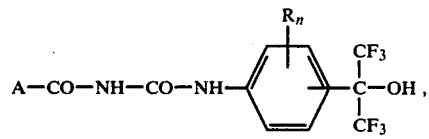

where A denotes a phenyl, thienyl or pyridyl-3 radical which is mono- or polysubstituted by halogen, linear or branched alkyl of 1 to 4 carbon atoms, or linear or branched alkoxy of 1 to 4 carbon atoms, R denotes linear or branched alkyl of 1 to 4 carbon atoms or linear or branched alkoxy of 1 to 4 carbon atoms, and n denotes one of the integers 0, 1 and 2, which have an insecticidal and acarididal action, and a process for combating insects and mites with these active ingredients.

5 Claims, No Drawings

AROYLUREAS

The present invention relates to aroylureas, a process for their manufacture, insecticidal and acaricidal agents containing these ureas as active ingredients, and a process for combating insects and mites with these active ingredients.

Insecticidally effective N-benzoyl-N'-phenylureas have been disclosed (German Laid-Open Applications DE-OS No. 2,123,236, DE-OS No. 2,531,279 and DE-OS No. 2,601,780). These active ingredients bear, on the phenyl ring, in the main substituents from the halogen, alkyl, haloalkyl, haloalkoxy and haloalkylthio groups. They are suitable for combating insects, such as caterpillars and beetles.

Further, J. Agric, Food Chem., 26, 164–166, 1978, discloses that N-(2,6-difluorobenzoyl)-N'-pyridylureas inhibit growth in *Musca domestica* and *Spodoptera frugiperda*.

We have now found that aroylureas of the formula

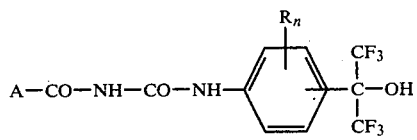

where A denotes a phenyl, thienyl or pyridyl-3 radical which is mono- or polysubstituted by halogen, linear or branched alkyl of 1 to to 4 carbon atoms, or linear or branched alkoxy of 1 to 4 carbon atoms, R denotes linear or branched alkyl of 1 to 4 carbon atoms or linear or branched alkoxy of 1 to 4 carbon atoms, and n denotes one of the integers 0,1 and 2, have strong insecticidal properties. Surprisingly, they also have an acaricidal action, and thus exhibit a property which has hitherto not been observed in the benzoylurea class of active ingredients.

In formula I, A denotes a phenyl, pyridyl-3 or thienyl radical (such as thienyl-3) which is mono- or polysubstituted by halogen, linear or branched alkyl of 1 to 4 carbon atoms, or linear or branched alkoxy of 1 to 4 carbon atoms. Examples of suitable substituents are fluorine, chlorine, bromine, methyl, ethyl, n-propyl, isopropyl, isobutyl, sec-butyl, methoxy, ethoxy, propoxy and pentoxy. Preferred substituents are fluorine, chlorine, methyl, and methoxy. The aromatic rings preferably bear up to 2 substituents.

R in formula I denotes linear or branched alkyl of 1 to 4 carbon atoms, e.g., methyl, ethyl, isopropyl, isobutyl, and sec-butyl, especially methyl, or linear or branched alkoxy of 1 to 4 carbon atoms, e.g., methoxy, ethoxy, n-propoxy, isopropoxy, and butoxy, preferably methoxy or ethoxy.

Preferred aroylureas of the formula I are those in which A denotes a phenyl, thienyl or pyridyl-3 radical which is mono- or disubstituted by halogen, and n is 0.

The aroylureas of the formula I may be obtained by reaction of isocyanates of the formula

A—CO—NCO     II, where A has the above meanings, with substituted anilines of the formula

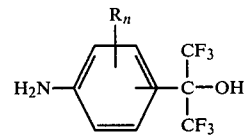

where R and n have the above meanings, in the presence of an inert organic solvent and at from 0° to 80° C.

Suitable inert organic solvents are aliphatic and aromatic, optionally chlorinated or nitrated hydrocarbons, such as benzene, toluene, xylenes, chlorobenzenes, gasoline, carbon tetrachloride, 1,2-dichloroethane, methylene chloride, chloroform, and nitromethane, acyclic and cyclic ethers, such as diethyl ether, dibutyl ether, tetrahydrofuran, and dioxane, acyclic and cyclic ketones, such as acetone, methyl ethyl ketone, methyl isopropyl ketone, and cyclohexanone, and nitriles, such as acetonitrile and benzonitrile. Mixtures of these solvents may also be used.

The reaction temperature may be varied within a wide range; it is generally from 0° to 80° C. Because the reaction is exothermic, it proceeds at from 20° to 60° C.

The reaction is generally carried out at atmospheric pressure.

To carry out the process, the components are preferably employed in equimolar ratios. No great advantage is to be gained by using an excess of either component. Generally, the substituted aniline of the formula III, together with the solvent or diluent, is placed in the reactor, and the isocyanate of the formula II is added. The reaction proceeds practically quantitatively. After a reaction period of several hours, as a rule after 2 hours, the product is filtered and dried under reduced pressure.

The compounds according to the invention are obtained as solids which are as a rule analytically pure; if they are not, they can be purified by recrystallization. They are characterized by elemental analysis and melting point.

The isocyanates of the formula II may be prepared by reaction of the corresponding primary amides with oxalyl chloride in accordance with the following equation, in which A has the above meanings:

A—CO—NH$_2$+Cl—CO—CO—Cl→A—CO—N-CO+CO+2HCl (J.Org.Chem., 28, 1805–1811, 1963).

The substituted anilines of the formula III are known or may be manufactured by the process described in J.Org.Chem., 30, 1001–1003, 1965, by reaction of hexafluoroacetone with an aniline of the formula

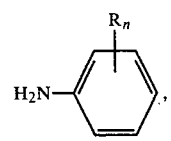

where R and n have the above meanings.

The aroylureas of the formula I may also be obtained by reaction of amides of the formula A—CO—NH$_2$, where A has the above meanings, with isocyanates of the formula

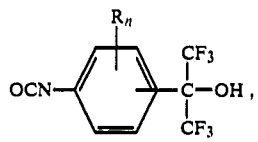

where R and n have the above meanings. The reaction may be carried out in pyridine in the presence of a catalytic amount of sodium at from 40° to 120° C., or in tetrahydrofuran with sodium hydride as base at from −20° C. to the reflux temperature of the solvent.

The following examples illustrate the production of the aroylureas of the formula I according to the invention.

EXAMPLE 1

0.055 mole of 2,6-difluorobenzoyl isocyanate is dripped into 0.05 mole of 4-(1-hydroxy-1-trifluoromethyl-2,2,2-trifluoroethyl)-aniline in 150 ml of absolute toluene. The temperature rises to 27° C. The mixture is heated for 3 hours at 50° C. and then filtered while hot, and the filter cake is dried under reduced pressure at 50° C. There is obtained 19.5 g (95% of theory) of N-(2,6-difluoro-benzoyl)-N'-[4-(1-hydroxy-1-trifluoromethyl-2,2,2-trifluoroethyl)-phenyl]-urea; m.p.: 205°–207° C.

|  | C | H | N | F |
|---|---|---|---|---|
| calc.: | 46.17 | 2.28 | 6.33 | 34.37 |
| found: | 46.1 | 2.4 | 6.1 | 34.4 |

EXAMPLE 2

0.04 mole of 4-chlorothenoyl-3-isocyanate in 30 ml of toluene is dripped into 0.035 mole of 4-(1-hydroxy-1-trifluoromethyl-2,2,2-trifluoroethyl)-aniline in 100 ml of absolute toluene. The temperature rises to 35° C. After the mixture has been stirred for 3 hours at 50° C., the precipitate is filtered off while warm, washed with ether, and dried under reduced pressure at 50° C. There is obtained 11.8 g (76% of theory) of analytically pure N-(4-chlorothenoyl-3)-N'-[4-(1-hydroxy-1-trifluoromethyl-2,2,2-trifluoroethyl)-phenyl]-urea; m.p.: 176°–179° C.

|  | C | H | N | S | Cl | F |
|---|---|---|---|---|---|---|
| calc.: | 40.3 | 2.0 | 6.3 | 7.2 | 7.9 | 25.5 |
| found: | 40.4 | 2.1 | 6.3 | 7.8 | 8.0 | 24.1 |

The following compounds for instance may be synthesized analogously:

A—CO—NH—CO—NH—[phenyl ring with positions 2,3,4,5,6 and B substituent]—C(CF₃)(CF₃)—OH

| No. | A | B(=Rₙ) | m.p. (°C.) |
|---|---|---|---|
| 3 | 2,6-dichlorophenyl | — | 221–224 |
| 4 | 2-chlorophenyl | — | 175–177 |
| 5 | 2,4-dichlorophenyl | — | 200–202 |
| 6 | 4-methylphenyl | — | 225–231 |
| 7 | pyridyl-Cl | — | 196–198 |
| 8 | 2-methylphenyl | — | 208–213 |
| 9 | 3-chlorophenyl | — | 199–201 |
| 10 | 4-bromophenyl | — | 197–201 |
| 11 | 2-chlorophenyl | 2-methyl | 175–177 |
| 12 | 2,5-dichlorophenyl | 2,5-dimethyl | 230–232 |
| 13 | 2,6-difluorophenyl | 2,6-dimethyl | 229–232 |
| 14 | 3-chlorophenyl | 2,6-dimethyl | 214–217 |
| 15 | 4-bromophenyl | 2,6-dimethyl | 242–244 |
| 16 | 2,6-difluorophenyl | 3-methyl | 139–142 |
| 17 | 2,6-dichlorophenyl | 3-methyl | 121–123 |
| 18 | 2,3-dichlorophenyl | — | 199–203 |
| 19 | 2,6-difluorophenyl | 2-methoxy | 195–197 |

| # | Aryl | R | mp (°C) |
|---|---|---|---|
| 20 | 2,3-dichlorophenyl | 2,6-dimethyl | 233–237 |
| 21 | 2,4-dichlorophenyl | 2,6-dimethyl | |
| 22 | 2-chlorophenyl | 2,6-dimethyl | 199–203 |
| 23 | 4-methylphenyl | 2,6-dimethyl | |
| 24 | 2-methylphenyl | 2,6-dimethyl | |
| 25 | 2,6-difluorophenyl | 2,5-dimethyl | 228–231 |
| 26 | 2,4-dichlorophenyl | 2,5-dimethyl | |
| 27 | 2-chlorophenyl | 2,5-dimethyl | |
| 28 | 2,3-dichlorophenyl | 2-methyl | 212–218 |
| 29 | 2,4-dichlorophenyl | 2-methyl | 223–226 |
| 30 | 4-methylphenyl | 2-methyl | 211–213 |
| 31 | 2-methylphenyl | 2-methyl | |
| 32 | 2,6-difluorophenyl | 2-methyl | 171–174 |
| 33 | 4-bromophenyl | 2-methyl | |
| 34 | 4-methylphenyl | 2-methyl | |
| 35 | 2-bromophenyl | — | 194 |
| 36 | 2-fluorophenyl | — | 150–154 |
| 37 | 2-bromophenyl | 2-methyl | 168–171 |
| 38 | 2-fluorophenyl | 2-methyl | 172–176 |
| 39 | 2-fluorophenyl | 2-ethyl | 135–137 |
| 40 | 2-bromophenyl | 2-ethyl | 162–168 |
| 41 | 2-bromophenyl | 2-isopropyl | |
| 42 | 2-fluorophenyl | 2-isopropyl | 149–156 |
| 43 | 2,3-dichlorophenyl | 2-ethyl | 205–208 |
| 44 | 2,3-dichlorophenyl | 2-isopropyl | 156–160 |
| 45 | 2,6-difluorophenyl | 2-ethyl | 175–179 |
| 46 | 2,6-difluorophenyl | 2-isopropyl | 140–143 |
| 47 | 2-fluoro-3-pyridyl | — | |
| 48 | 2-fluoro-3-pyridyl | 2-methyl | |
| 49 | 4-methylphenyl | 2,5-dimethyl | 187–189 |
| 50 | 3-chlorophenyl | 2-methyl | 224–226 |
| 51 | 2,3-dichlorophenyl | 2-methoxy | 135–138 |
| 52 | 2-fluorophenyl | 2-methoxy | 164–167 |

| No. | A | B(=R_n) | m.p. (°C.) |
|---|---|---|---|
| 53 | 2-chlorophenyl | 2-methoxy | 163–166 |
| 54 | 2-bromophenyl | 2-methoxy | — |
| 55 | 3-bromo-2-pyridyl | | — |
| 56 | 2,6-dichloro-3-pyridyl | | — |
| 57 | 2,4-dichloro-3-pyridyl | | — |
| 58 | 2-chloro-3-pyridyl | 2-methoxy | — |
| 59 | 3-pyridyl | | — |
| 60 | 3-pyridyl | 2-methyl | — |
| 61 | 3-thienyl | | — |
| 62 | 3-thienyl | 2-methyl | — |
| 63 | 2,3-dichloro-4-thienyl | | — |
| 64 | 2,5-dibromo-3-thienyl | | — |
| 65 | 2,3-dichloro-4-thienyl | 2-methyl | — |
| 66 | 2,3-dichlorophenyl | 4-methyl | 143–148 |
| 67 | 2,3-difluorophenyl | 4-methyl | 143–150 |
| 68 | 2-chlorophenyl | 4-methyl | 160–169 |
| 69 | 2-bromophenyl | 4-methyl | — |
| 70 | 2,5-dichlorophenyl | 4-methyl | — |
| 71 | 2-methylphenyl | 4-methyl | — |
| 72 | 2-fluorophenyl | 4-methyl | 194–196 |
| 73 | 2,3-dichlorophenyl | 4-ethyl | 170–178 |
| 74 | 2,3-difluorophenyl | 4-ethyl | 98–106 |
| 75 | 2-chloro-3-pyridyl | 4-methyl | 196–197 |
| 76 | 2-chloro-3-pyridyl | 4-ethyl | — |
| 77 | 2-fluoro-3-pyridyl | 4-methyl | — |
| 78 | 2-fluoro-3-pyridyl | 4-ethyl | — |
| 79 | 2,3-dichloro-4-thienyl | 4-methyl | — |

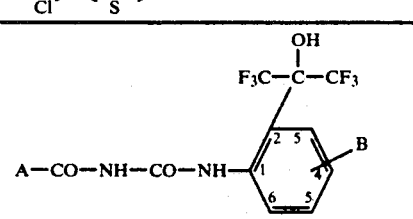

A—CO—NH—CO—NH—[phenyl with OH, F₃C—C—CF₃ substituent and B]

-continued

| | | | |
|---|---|---|---|
| 80 | 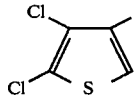 | 4-ethyl | |
| 81 | 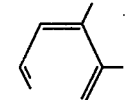 | 4-methyl | |
| 82 | 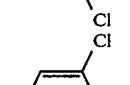 | 4-ethyl | |
| 83 | 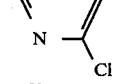 | 4-methyl | 152–156 |
| 84 | 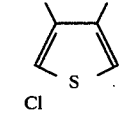 | 4-ethyl | 150–158 |
| 85 | 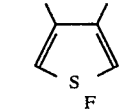 | 5-methyl | 140–142 |
| 86 | 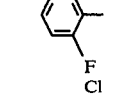 | 5-methyl | 121–123 |

The compounds according to the invention are suitable for effectively combating pests from the class of insects and mites.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argrillacea, Lymantria dispar., Lymantria monocha, Pieris brassicae,* and *Aporia crataegi.*

Examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hipposcastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus,* Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus, Blastophagus piniperda, and cockroaches, such as *Blatta germanica, Periplaneta americana, Blatta orientalis, Blaberus giganteus,* and *Blaberus fuscus.*

Examples from the Diptera order are *Musca domestica, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae,* and *Pegomya hyoscyami.*

Examples from the Hymenoptera order are *Athalia rosae, Haplocampa minuta, Monomorium pharaonis, Solenopsis geminata,* and *Atta sexdens.*

Examples from the Heteroptera order are *Nezara viridula, Eurygaster integriceps, Blissus leucopterus, Dysdercus cingulatus, Dysdercus intermedius, Piesma quadrata,* and *Lygus pratensis.*

Examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii.*

An example from the Isoptera order is *Reticulitermes lucifugus.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

The compounds according to the invention may be successfully employed as pesticides for crop protection, and in the hygiene, stores protection and veterinary sectors.

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethylsulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95% of active ingredient, or even the 100% active ingredient.

Examples of formulations are given below.

I. 3 parts by weight of N-(2-chlorobenzoyl)-N'-[4-(1-hydroxy-1-trifluoromethyl-2,2,2-trifluoroethyl)-phenyl]-urea is intimately mixed with 97 parts by weight of particulate kaolin. A dust is obtained containing 3% by weight of the active ingredient.

II. 30 parts by weight of N-(2,6-dichlorobenzoyl)-N'-[4-(1-hydroxy-1-trifluoromethyl-2,2,2-trifluoroethyl)-phenyl]-urea is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of N-(2,4-difluorobenzoyl-N'-[4-(1-hydroxy-1-trifluoromethyl-2,2,2-trifluoroethyl)-phenyl]-urea is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dedecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of N-(4-bromobenzoyl-N'-[4-(1-hydroxy-1-trifluoromethyl-2,2,2-trifluoroethyl)-phenyl]-urea is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows:
1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-4-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethylpyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphorylimionphenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O,-diethyl-O-(2-pyrazinyl)-phosphorothioate, O,O-diethyl-O-[2-isopropyl-4-methylpyrimidinyl-(6)]-phosphorothioate, O,O-dietyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanearboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl- -isopropyl-4-chlorophenylacetate.

The following examples demonstrate the biological action of the new compounds. The agents used for comparison purposes are N-(2,6-difluorobenzoyl)-N'-(4-chlorophenyl)-urea (I; German Laid-Open Application DE-OS No. 2,123,236) and N-(2,6-difluorobenzoyl)-N'-(5-chloropyridyl-2)-urea (II; J.Agric. Food Chem., 26, 164–166, 1978). The numbers of the active ingredients are the same as in the manufacturing examples and the tables following them.

EXAMPLE A

Experiments with counted females of the spider mite (*Tetranychus telarius*)

In a spray booth, potted bushbeans are sprayed to runoff on a rotating disc with aqueous formulations of the active ingredients. After the sprayed layer has dried, pieces 25 mm in diameter are punched from the leafblades. They are placed on cellulose material, the edges of which hang in water.

10 adult females are placed on each punched leaf disc. The action is assessed after 6 days, eggs, larvae and adults being counted.

| Active ingredient no. | Concentration of active ingredient formulation (wt %) | No. of eggs laid within 6 days | No. hatched |
|---|---|---|---|
| 1 | 0.1 | 5 | 0 |
|   | 0.05 | 7 | 0 |
|   | 0.02 | 35 | 0 |
|   | 0.01 | 35 | 0 |
| 2 | 0.1 | 3 | 0 |
|   | 0.05 | 4 | 0 |
|   | 0.025 | 7 | 0 |
| 3 | 0.1 | 5 | 2 |
| 4 | 0.05 | 2 | 0 |
| 5 | 0.1 | 17 | 0 |
|   | untreated | 75 | 55 |

EXAMPLE B

Action on larvae of the flour moth (*Ephestia kuehniella*); breeding experiment

Wheat flour heavily infested with eggs of the flour moth is intimately mixed with the active ingredients. 10 g of the mixture is filled into 250 ml bottles, which are then kept at 22° C.

The development of the larvae is assessed after 4 weeks.

| Active ingredient no. | Concentration of active ingredient in flour (ppm) | |
|---|---|---|
| 1 | 4 | considerable growth inhibition |
| I | 100 | growth inhibition |
| I | 50 | ineffective |

EXAMPLE C

Breeding experiment with mosquito larvae (*aedes aegypti*)

The active ingredient formulations are added to 200 ml of tapwater; 30 to 40 Aedes larvae in the 4th stage are then introduced.

The temperature is kept at 25° C. Pupation and hatching of the imagoes are assessed against an untreated control.

Feeding is carried out once during the experiment.

| Active ingredient no. | Concentration of active ingredient formulation (ppm) | Kill rate (%) |
| --- | --- | --- |
| 1 | 0.01 | 100 |
| 3 | 0.1 | 100 |
|   | 0.05 | considerable inhibition |
| 4 | 0.05 | 100 |
| 5 | 0.5 | 100 |

EXAMPLE D

Breeding experiment with *Tribolium castaneum*

10 g samples of wheat flour are carefully mixed with the active ingredient formulations, and the mixtures are introduced into 250 ml glass bottles. 20 beetles are then placed in each bottle for egg-laying. The beetles are sieved off after 14 days. The treated flour with the laid eggs is kept at 24° C. and observed until the next beetle generation hatches.

| Active ingredient no. | Concentration of active ingredient in flour (ppm) | |
| --- | --- | --- |
| 1 | 2.0 | total inhibition |
|   | 1.0 | considerable inhibition |
|   | 0.5 | inhibition |
| I | 2.0 | inhibition |
|   | 1.0 | ineffective |
| II | 100 | ineffective |

EXAMPLE E

Breeding experiment with *Drosophila melanogaster*

At 60° C., 40 ml of a bran nutrient agar is filled into 250 ml plastic bottles and intimately mixed with 2 ml of the aqueous active ingredient formulations.

After the agar has cooled, it is inoculated with a yeast suspension and a rolled-up filter paper is placed to lean against the inside of the bottle.

From 20 to 40 approximately 6-day old Drosophila are then introduced and the vessels capped.

Assessment takes place after 10 days.

| Active ingredient no. | Concentration of active ingredient in nutrient agar (ppm) | |
| --- | --- | --- |
| 1 | 5.0 | growth inhibition |
| 3 | 12.5 | growth inhibition |
| 4 | 25.0 | growth inhibition |
| II | 50.0 | growth inhibition |
|   | 25.0 | ineffective |

We claim:

1. An aroylurea of the formula

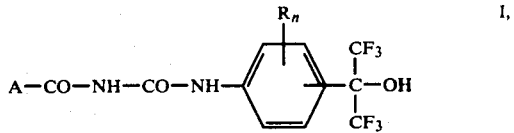

where A denotes a phenyl radical which is mono- or polysubstituted by halogen, linear or branched alkyl of 1 to 4 carbon atoms, or linear or branched alkoxy of 1 to 4 carbon atoms, R denotes linear or branched alkyl of 1 to 4 carbon atoms or linear or branched alkoxy of 1 to 4 carbon atoms, and n denotes one of the integers 0,1 and 2.

2. An aroylurea of the formula I as claimed in claim 1, wherein A denotes a phenyl radical which is mono- or disubstituted by halogen and n is 0.

3. N-(2-chlorobenzoyl)-N'-[4'-(1-hydroxy-1-trifluoromethyl-2,2,2-trifluoroethyl)-phenyl]-urea.

4. N-(2,6-difluorobenzoyl)-N'-[4'-(1-hydroxy-1-trifluoromethyl-2,2,2-trifluoroethyl)-phenyl]-urea.

5. N-(2,6-dichlorobenzoyl)-N'-[4'-(1-hydroxy-1-trifluoromethyl-2,2,2-trifluoroethyl)-phenyl]-urea.

* * * * *